United States Patent
Marnay et al.

(10) Patent No.: US 9,655,742 B2
(45) Date of Patent: May 23, 2017

(54) SPINAL INTERVERTEBRAL IMPLANT

(71) Applicant: PROSTEEL, Ramonville-Saint-Agne (FR)

(72) Inventors: Thierry Marnay, Montepellier (FR);
Jean-François Limito, Balma (FR);
Eric Zambiasi, Cugnaux (FR)

(73) Assignee: PROSTEEL, Ramonville-Saint-Agne (FR)

( * ) Notice: Subject to any disclaimer, the term of this patent is extended or adjusted under 35 U.S.C. 154(b) by 344 days.

(21) Appl. No.: 14/358,486

(22) PCT Filed: Nov. 19, 2012

(86) PCT No.: PCT/FR2012/000468
§ 371 (c)(1),
(2) Date: May 15, 2014

(87) PCT Pub. No.: WO2013/072582
PCT Pub. Date: May 23, 2013

(65) Prior Publication Data
US 2014/0336771 A1    Nov. 13, 2014

(30) Foreign Application Priority Data
Nov. 17, 2011   (FR) ..................................... 11 60462

(51) Int. Cl.
*A61F 2/44*    (2006.01)
*A61F 2/30*    (2006.01)

(52) U.S. Cl.
CPC .............. *A61F 2/4455* (2013.01); *A61F 2/44* (2013.01); *A61F 2/447* (2013.01);
(Continued)

(58) Field of Classification Search
CPC .................................................... A61F 2/4455
See application file for complete search history.

(56) References Cited

U.S. PATENT DOCUMENTS

| 2010/0217393 A1* | 8/2010 | Theofilos .............. A61F 2/4455 |
| | | 623/17.11 |
| 2011/0098747 A1 | 4/2011 | Donner et al. |
| 2011/0301714 A1 | 12/2011 | Theofilos |

FOREIGN PATENT DOCUMENTS

| EP | 2368528 A1 | 9/2011 |
| FR | 2727003 A1 | 5/1996 |

(Continued)

*Primary Examiner* — Andrew Yang
(74) *Attorney, Agent, or Firm* — Seed IP Law Group LLC

(57) ABSTRACT

An intervertebral spinal implant, for insertion between two consecutive vertebral bodies, includes a volume, inclined first and second through-holes formed in the volume, and elongated first and second fastening elements for securing the volume. The first and second through-holes have respective ends that open onto a front face and onto lower and upper faces of the volume, respectively. The first fastening element extends through the first through-hole and is implanted in the vertebral body adjacent to the lower face. The second fastening element extends through the second through-hole and is implanted in the vertebral body adjacent to the upper face. The through-holes intersect such that one of the fastening elements secures the other fastening element, once the fastening elements are respectively in place in the through-holes.

20 Claims, 13 Drawing Sheets

(52) U.S. Cl.
CPC ............... *A61F 2002/30607* (2013.01); *A61F 2002/30616* (2013.01); *A61F 2002/30782* (2013.01); *A61F 2002/30785* (2013.01); *A61F 2002/30787* (2013.01); *A61F 2002/30904* (2013.01); *A61F 2002/4475* (2013.01); *A61F 2310/00023* (2013.01)

(56) References Cited

FOREIGN PATENT DOCUMENTS

| | | |
|---|---|---|
| FR | 2982764 A1 | 5/2014 |
| GB | 2454229 A | 5/2009 |
| WO | 2010/121028 A2 | 10/2010 |
| WO | 2011/080535 A1 | 7/2011 |
| WO | 2011/155931 A1 | 12/2011 |

* cited by examiner

Fig. 13
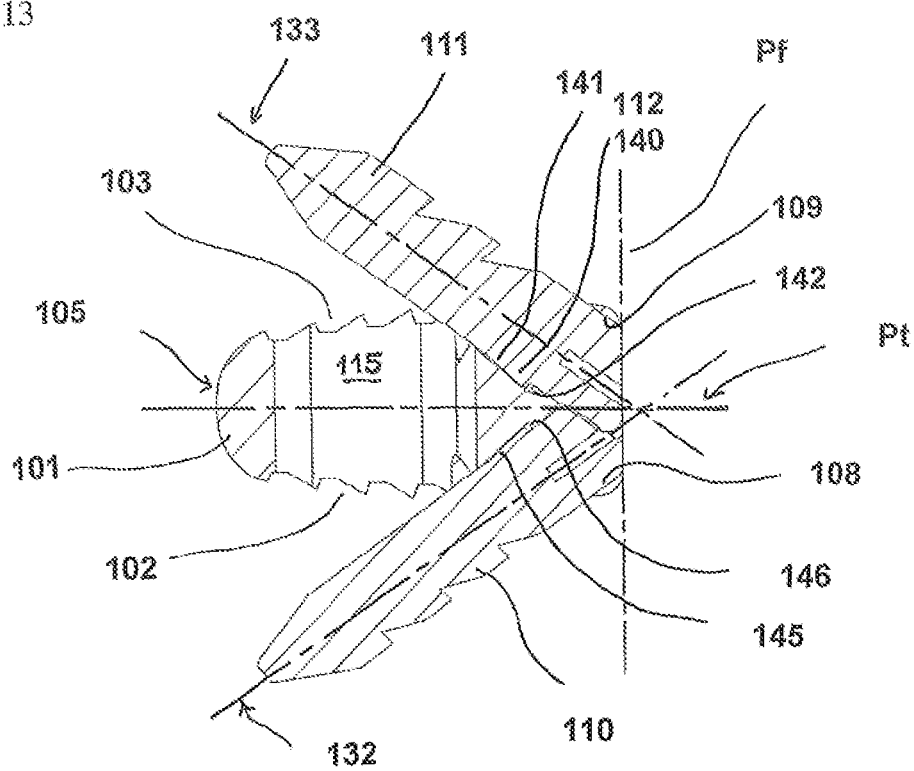
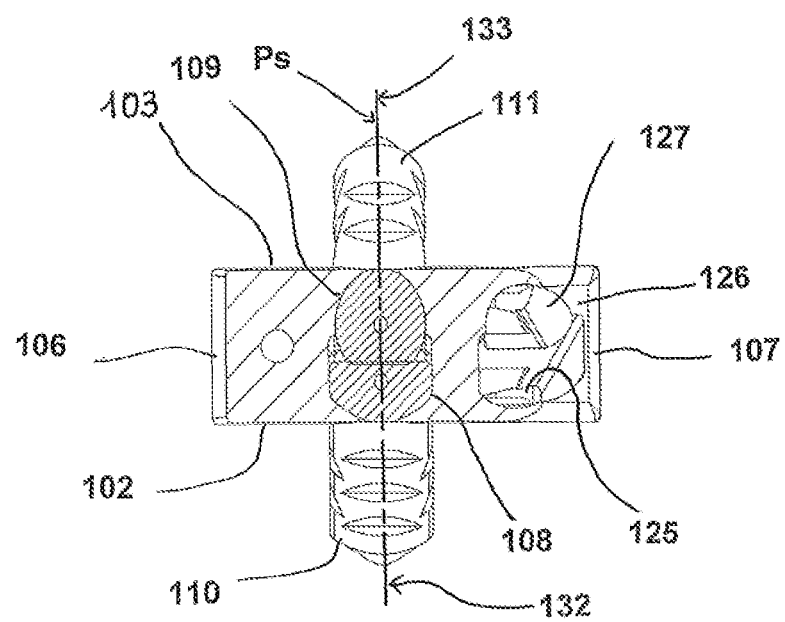
Fig. 14

Fig. 15
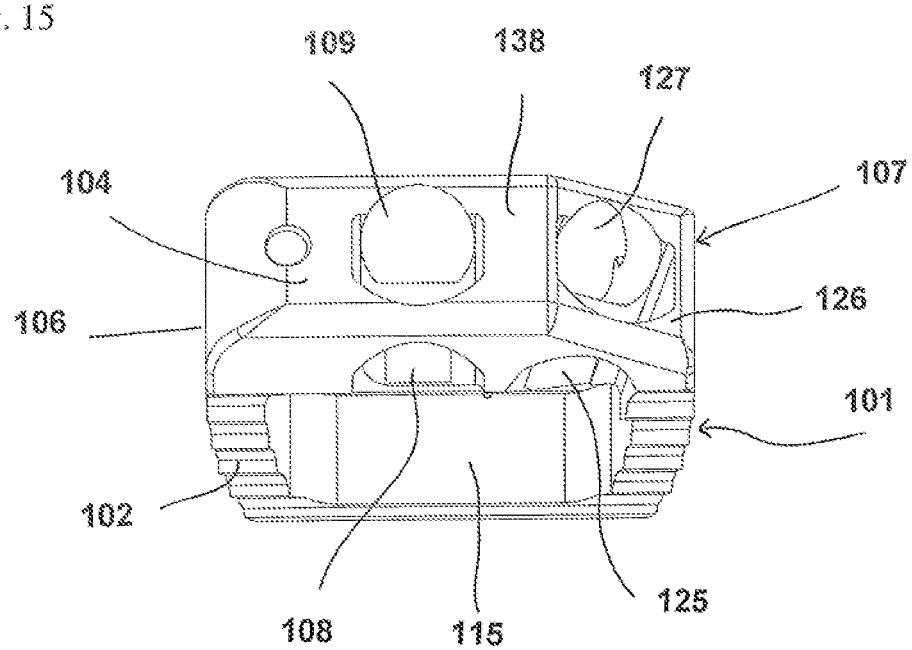
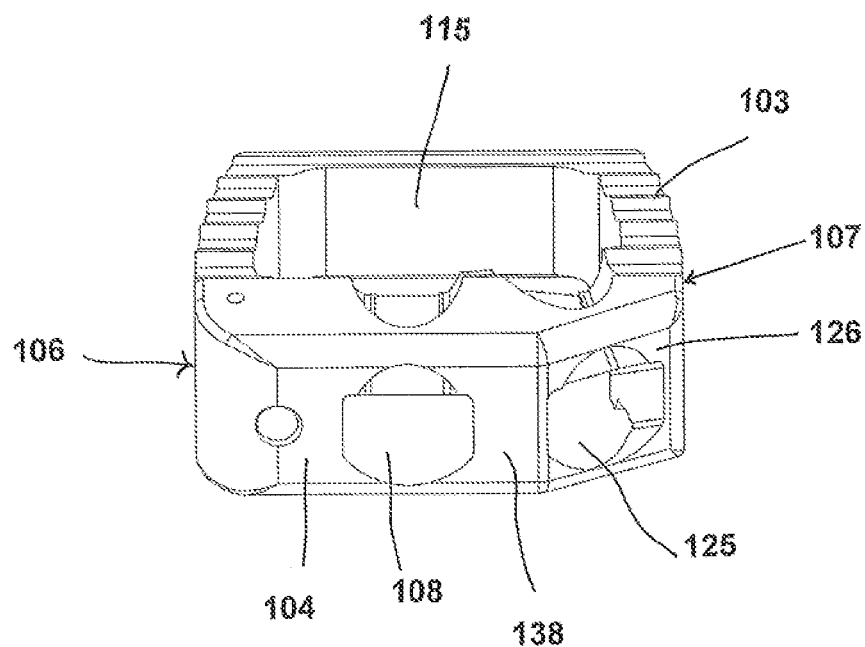
Fig. 16

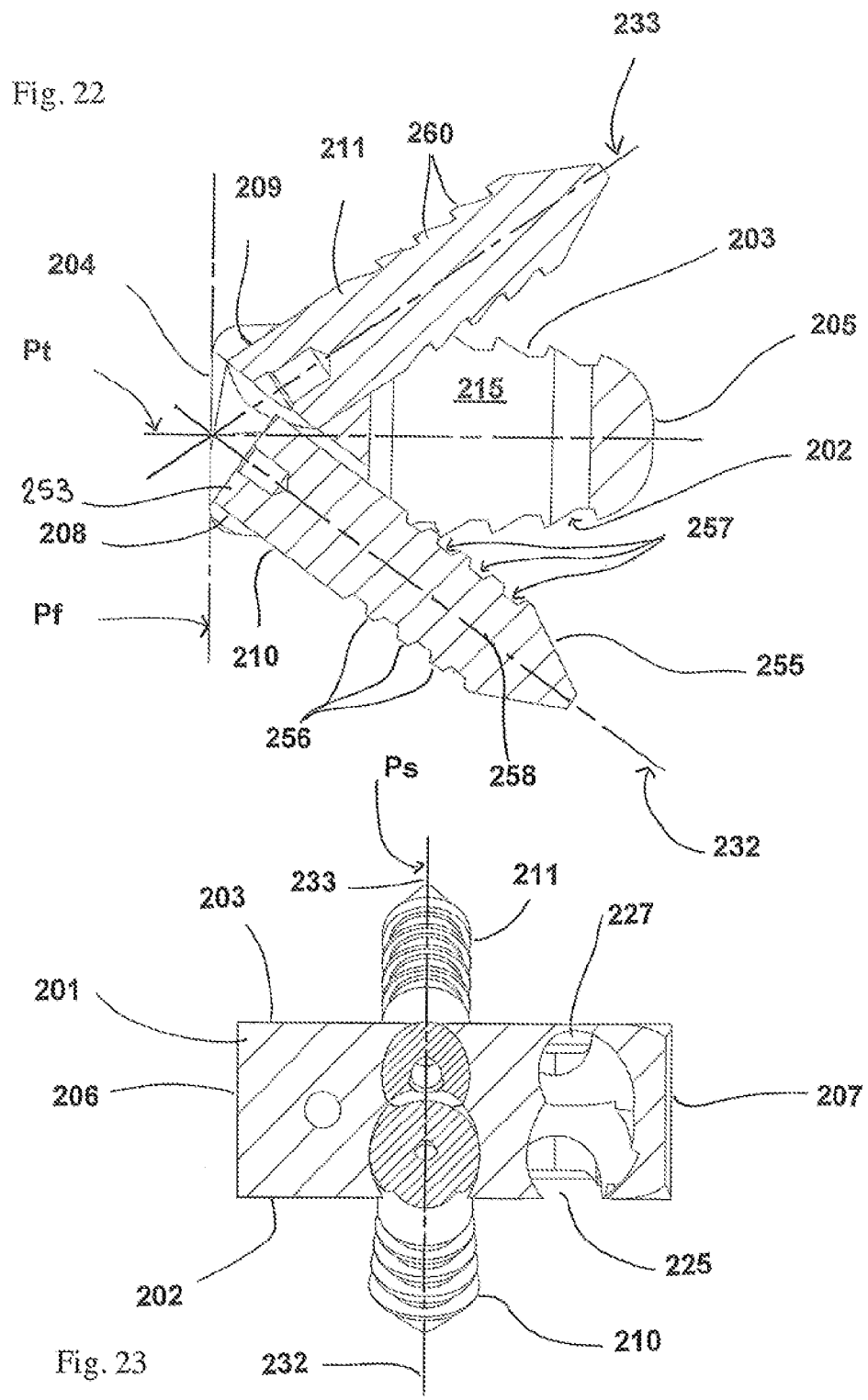

SPINAL INTERVERTEBRAL IMPLANT

The present invention relates to an intervertebral spinal implant intended for insertion between two successive vertebral bodies, comprising:
a volume defining at least:
  a lower face and an upper face, opposite one another so as to be placed in contact with the two successive vertebral bodies respectively,
  a front face, a rear face, and two side faces, connecting the two lower and upper faces,
a first inclined through-hole formed in the volume so that its two ends respectively open onto the front face and the lower face of the volume,
a second inclined through-hole formed in the volume so that its two ends respectively open onto the front face and the upper face of the volume,
a first elongated fastening element for securing the volume, its length being greater than that of the first inclined hole, able to cooperate by longitudinal insertion into said hole from the front in order to be implanted in the vertebral body adjacent to the lower face of the volume,
a second elongated fastening element for securing the volume, its length being greater than that of the second inclined hole, able to cooperate by longitudinal insertion into said hole from the front in order to be implanted in the vertebral body adjacent to the upper face of the volume.

The prior art teaches such implants, generally known as interbody fusion cages. Such implants are primarily intended to allow the fusion of the two vertebrae the implant is placed between. The cage typically has a central housing that opens to the upper and lower faces of the cage and which houses a graft for fusing the two bodies. There are cervical and lumbar interbody fusion cages. The interbody fusion cage is intended for implantation in place of the intervertebral disc.

Such implants are known for example from patents FR 2727003 and EP 2368528.

One problem with such implants is retaining the fastening elements in place once they have been inserted into the vertebral bodies. In general, these fastening elements can be a screw which is implanted by screwing it into place, or a pin, rod, or similar body having a penetrating end which is implanted by driving it into the vertebral bodies through their housing inside the cage. The advantage of a screw-type fastening element lies in its capacity to remain in its housing once implanted, but the disadvantage is that the installation time is relatively long because of the rotational movement required to screw in all the fastening elements. An advantage of a pin, rod, or similar fastening element is that it is quickly installed in a fast and simple translational movement, but a disadvantage is the fact that the fastening element can be driven from its housing by a reverse movement after placement, in particular before the two vertebrae are fused together by the graft.

The applicant has created a cage intended for intercervical implantation, fastened by rods inserted into the vertebral bodies, which are screwed into their housing in the cage by means of a front plate which is clipped in place onto the cage and covers the heads of the fastening rods in order to prevent any reverse movement of the rods after they have been implanted. However, placement of this front plate to secure the rods can be problematic in some applications, especially lumbar intervertebral applications where anterior access is not easy because of the presence of blood vessels in the anterior area of the lumbar vertebrae.

The present invention essentially overcomes these disadvantages. More specifically, it consists of an intervertebral spinal implant as defined above, characterized in that said first and second inclined through-holes intersect so that one of said first and second elongated fastening elements constitutes a first locking means for securing the other of said first and second elongated fastening elements, once said first and second elongated fastening elements are respectively in place in the first and second inclined holes.

Thus, according to the invention, at least one of the fastening elements locks the other in place so that the fastening element which is locked by the other can be a body which is slid into place, such as a rod, and is therefore quickly implanted, while benefiting from being automatically locked in place when the other fastening element is implanted, thereby providing rapid installation while offering an effective locking system for at least one of the fastening elements without requiring additional time and without the need for an additional locking member. The first and second inclined holes may open onto an anterofrontal portion of the front face of the volume for anterofrontal implantation of the fastening elements, or onto an anterolateral portion of said face for anterolateral implantation of the fastening elements.

According to an advantageous characteristic, the intervertebral spinal implant according to the invention further comprises:
a third inclined through-hole formed in the volume so that its two ends respectively open onto an anterolateral portion of said front face and onto said lower face of the volume,
a fourth inclined through-hole formed in the volume so that its two ends respectively open onto said anterolateral portion of said front face and onto said upper face of the volume,
said third and fourth inclined through-holes intersect such that said one of said first and second elongated fastening elements constitutes a first locking means for securing the other of said first and second elongated fastening elements, once said first and second elongated fastening elements are respectively in place in said third and fourth inclined holes.

This characteristic offers the additional possibility of anterolateral implantation of the fastening elements in two additional holes arranged anterolaterally in the volume, when anterofrontal implantation of the fastening elements in the first and second anterofrontal holes is not possible or is more difficult.

According to an advantageous characteristic, said one of the first and second elongated fastening elements constitutes a first locking means for securing the other of said first and second elongated fastening elements, once said first and second elongated fastening elements are respectively in place in the first and second inclined through-holes, or respectively in place in the third and fourth inclined through-holes, via a first interlocking connection, said one of said first and second elongated fastening elements acting as a stop for the other of said first and second elongated fastening elements, preventing it from backward longitudinal movement.

According to an advantageous characteristic, the intervertebral spinal implant according to the invention further comprises a second locking means for securing, in the volume, said one of the first and second elongated fastening elements constituting said first locking means for securing the other of said first and second elongated fastening elements, once said first and second elongated bodies are respectively in place in the first and second inclined holes, or respectively in place in the third and fourth inclined through-holes.

According to an advantageous characteristic, said second locking means comprises a frictional connection of said one of the first and second elongated fastening elements to the other of said first and second elongated fastening elements.

According to an advantageous characteristic, an alternative to the previous one, said second locking means comprises a form-locking connection of said one of the first and second elongated fastening elements to the volume or to the other of said first and second elongated fastening elements.

According to an advantageous characteristic, an alternative to the previous one, said second locking means comprises an interlocking connection obtained by a quarter-turn rotation about its longitudinal axis of said one of the first and second elongated fastening elements after it is inserted longitudinally into its inclined through-hole, thus locking said one of the first and second elongated fastening bodies into this position in the volume.

According to an advantageous characteristic concerning the second locking means based on a frictional connection, said second locking means comprises a through-hole created in said one of the first and a second elongated fastening elements, which is aligned with the inclined through-hole into which the other of said first and second elongated fastening elements is inserted, when said one of the first and second elongated fastening elements is inserted into its inclined through-hole so as to be in abutment.

According to an advantageous characteristic of the previous one, said second locking means comprises a conical assembly consisting of:
said through-hole, which is conical in shape, created in said one of the first and second elongated fastening elements, and
a conical head created at one end of the other of said first and second elongated fastening elements.

According to an advantageous characteristic, at least one of said first and second elongated fastening elements consists of a screw.

According to an advantageous characteristic of the previous one, one of said first and second elongated fastening elements consists of a pin to be inserted longitudinally, and the other of said first and second elongated fastening elements consists of a screw, said through-hole being created in the pin-type elongated fastening element.

The pin to be inserted is here an elongated fastening element which comprises an insertion end for example of known type, suitable for penetrating a bony vertebral body, for example an end that is tapered, V-shaped, conical, or some similar shape, ending substantially in an edge, a point, or similar.

According to an advantageous characteristic of the previous one, said insertion pin comprises a radial slot opening into said through-hole of the pin, such that when the screw is inserted into its inclined hole, the portions of the pin forming the through-hole move apart at the end of the screwing process due to the pressure of the conical assembly between the conical head of the screw and the conical hole of the pin, pressing them against the volume.

According to a second advantageous characteristic concerning the locking means based on a form-locking connection, said first and second elongated fastening elements are composed of first and second insertion pins, said form-locking connection being achieved by means of a retaining member formed in relief on the second insertion pin and which extends transversely beyond the free passage section, in the volume, of the second insertion pin when the first pin is in its end-of-insertion position, so as to provide a slight resistance to insertion, said retaining member being designed so that it is able to:
deform elastically with the assembly consisting of the volume and the first and second insertion pins during insertion of the second pin, so that the retaining member and the second pin which carries it pass through said free passage section, and
cooperate at the end of insertion with a stop formed on the volume, the assembly consisting of the volume and the first and second insertion pins having elastically returned to its initial undeformed shape.

At the end of insertion, said stop formed on the volume cooperates with said retaining member to prevent inadvertent rearward longitudinal displacement of the second pin corresponding to an inverse movement of the pin when the fastening pin is inserted. "First and second insertion pins" is understood to mean the order in which the fastening pins are inserted into the cage, it being understood that the first pin to be inserted can correspond to the first or second fastening element, depending on requirements; the same is true for the second insertion pin.

According to an advantageous characteristic concerning the second locking means based on an interlocking connection, one of said first and second elongated fastening elements consists of a first insertion pin, and the other of said first and second elongated fastening elements consists of a second insertion pin, this second pin being provided with a head constituting the interlocking connection in cooperation with a seat in the volume within which the head is pivoted at the end of insertion, said head being provided with means for engaging said head for rotation.

According to an advantageous characteristic of the previous one, said head of the second pin has an elliptical cross-section.

According to an advantageous characteristic, said one of the first and second elongated fastening elements that is rotated a quarter turn about its longitudinal axis comprises an outer portion which extends outside the volume when it is in the inserted position and able to pivot within its inclined through-hole, said outer portion being adapted for insertion into the adjacent vertebral body and comprising:
a longitudinal central core,
a plurality of circumferential ribs each extending in a plane transverse to said longitudinal central core and their periphery forming an ellipse,
a plurality of cylindrical grooves, each between two successive circumferential ribs.

This characteristic provides a specific elongated fastening element which, irrespective of the application in the volume of the implant according to the invention, provides improved attachment in any bony element, the final quarter turn of the fastening element after insertion into a bony element providing synergistic compression of the bone in a region of said bone not directly affected by the longitudinal insertion of the fastening element. This increases the force retaining the fastening element in the bone, particularly in the longitudinal direction of the elongated fastening element, which is the direction of insertion. Such an elongated fastening element according to this characteristic can be applied in a conventional intervertebral spinal implant, as defined in the scope of the present invention established at the beginning of this document, to one and/or the other of the first and second fastening elements, the volume able to comprise for example separate and independent holes for each fastening element. In this specific application, the quarter-turn rotation about the longitudinal axis of the first or second elongated fastening element is done after said elongated element is inserted longitudinally into its inclined through-hole, locking said first or second elongated fastening element in this position in the volume. Such an elongated fastening element according to this characteristic consists, for example, of an insertion pin, said pin being provided with a head constituting the interlocking connection in cooperation with a seat in the volume in which said head, equipped with means for engaging it for rotation, is pivoted at the end of insertion.

According to an advantageous characteristic, the volume is in the form of an intervertebral cage having a central housing opening onto the lower and upper faces, adapted to house a graft in contact with the two successive vertebral bodies which said intervertebral spinal implant is intended to be inserted between.

In a known manner, the graft allows obtaining interbody fusion between the two successive vertebrae where the cage is implanted.

Other features will be apparent from the following description of several exemplary embodiments of an intervertebral spinal implant according to the invention, together with the accompanying drawings. These examples are provided as illustrations and are in no way limiting.

FIG. 13 represents a sagittal cross-sectional view of FIG. 11, along the longitudinal axis of the fastening elements.

FIG. 14 represents a front cross-sectional view of FIG. 11, at the heads of the fastening elements.

FIG. 15 represents a bottom perspective view along the axis of the second fastening hole, showing only the volume according to the second example of an implant shown in FIGS. 9-14.

FIG. 16 represents a top perspective view along the axis of the first fastening hole, showing only the volume according to the second example of an implant shown in FIGS. 9-14.

FIG. 22 represents a sagittal cross-sectional view of FIG. 19, along the longitudinal axis of the fastening elements.

FIG. 23 represents a front cross-sectional view of FIG. 19, at the heads of the fastening elements.

Figure 1:
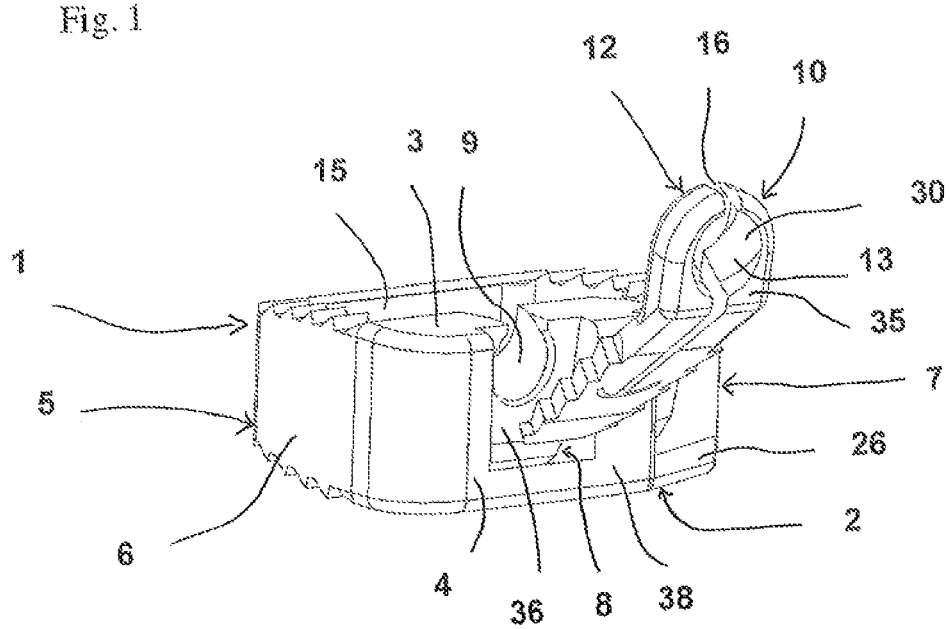
FIG. 1 shows a left anterolateral perspective view, partial and exploded, of a first exemplary embodiment of an intervertebral spinal implant according to the invention. The view is described as partial because only one of the fastening elements has been represented.

The intervertebral spinal implant illustrated in FIGS. 1 to 8 is intended for insertion between two successive vertebral bodies (not shown), particularly in the lumbar region between two lumbar vertebrae. The represented implant comprises:

a volume 1 or interbody fusion cage defining at least:
  a lower face 2 and an upper face 3, opposite one other so as to be placed in contact with the two successive vertebral bodies respectively,
  a front face 4, a rear face 5, and two side faces 6 and 7, connecting the two lower 2 and upper 3 faces.
a first 8 inclined through-hole formed in the volume 1 so that its two ends respectively open onto on the front face 4 and the lower face 2 of the volume 1,
a second 9 inclined through-hole formed in the volume 1 so that its two ends respectively open onto the front face 4 and the upper face 3 of the volume 1,
a first 10 elongated fastening element for securing the volume 1, its length being greater than that of the first inclined hole 8, able to cooperate by longitudinal insertion into said hole from the front in order to be implanted in the vertebral body adjacent to the lower face 2 of the volume 1, a second 11 elongated fastening element for securing the volume 1, its length being greater than that of the second 9 inclined hole, able to cooperate by longitudinal insertion into said hole from the front in order to be implanted in the vertebral body adjacent to the upper face 3 of the volume 1.

Figure 5:
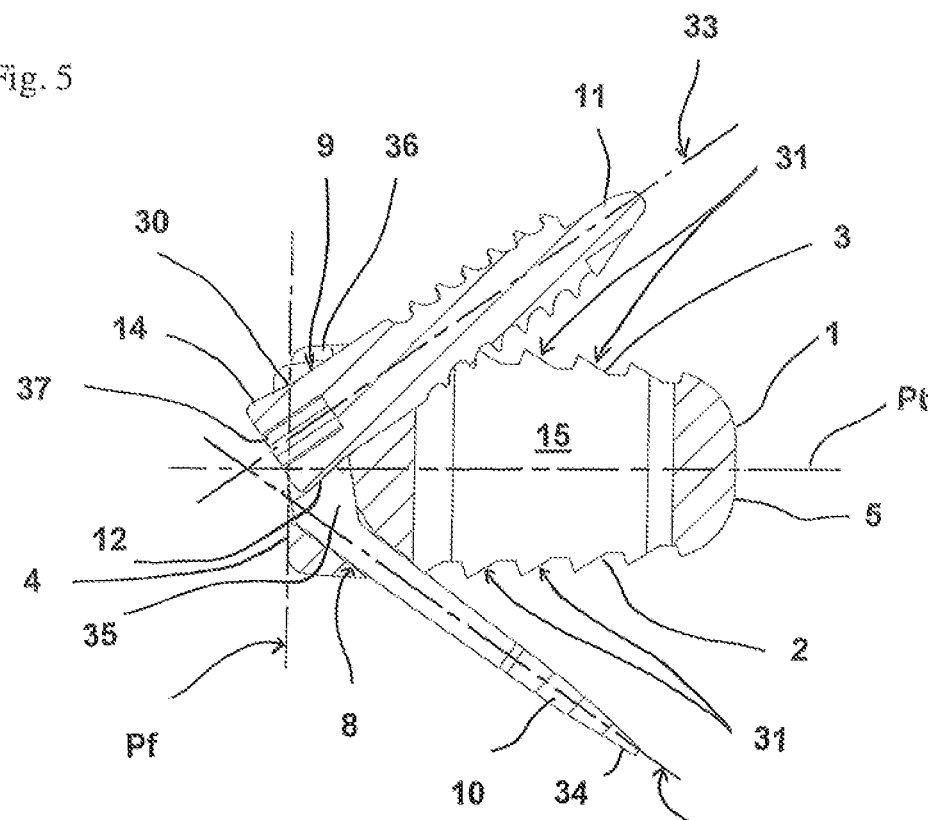
FIG. 5 represents a sagittal cross-sectional view of FIG. 3, along the longitudinal axis of the fastening elements.
Figure 6:
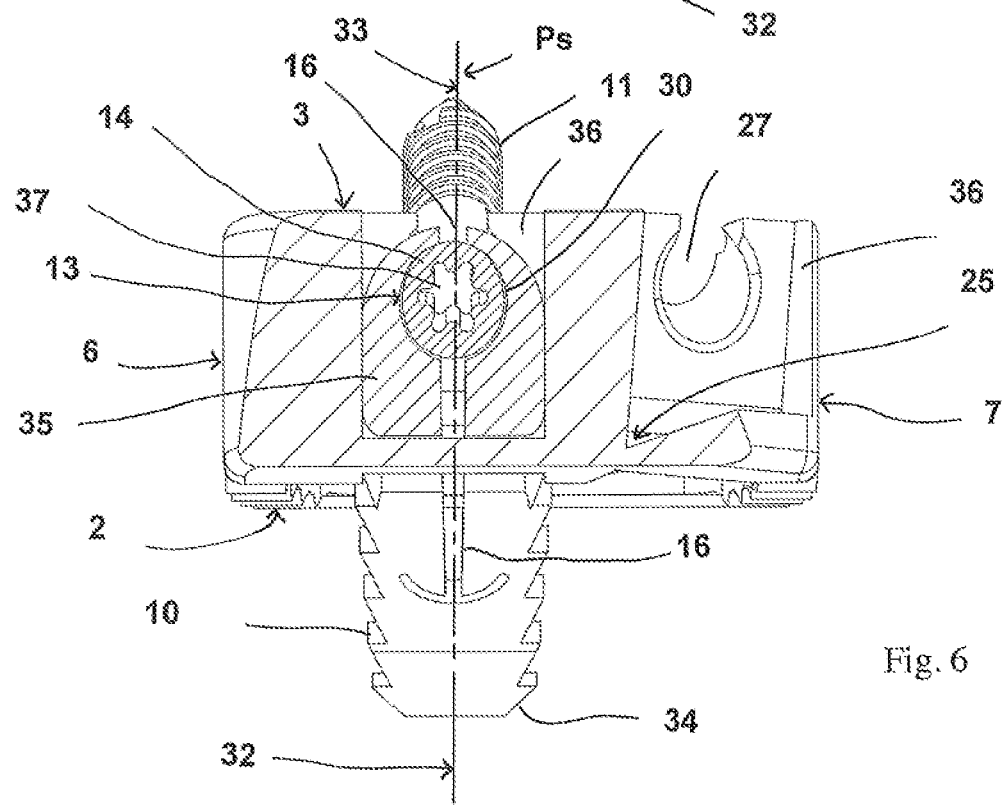
FIG. 6 represents a front cross-sectional view of FIG. 3, at the heads of the fastening elements.

Three planes perpendicular to each other are defined relative to the volume 1: a frontal plane Pf, a transverse plane Pt, and a sagittal plane Ps, for example as represented in FIGS. 5 and 6. Of course, planes parallel to those shown also lie within the above definition.

Figure 3:
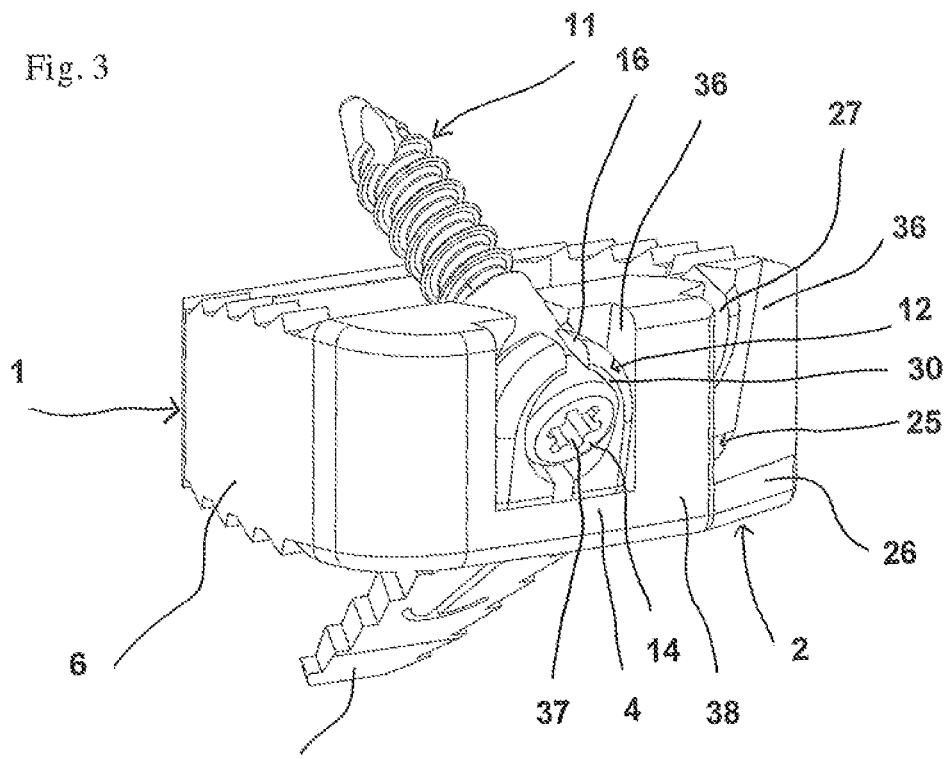
FIG. 3 represents a perspective view of FIG. 2, with both fastening elements shown in place in their respective anterofrontal housings in the volume.
Figure 4:
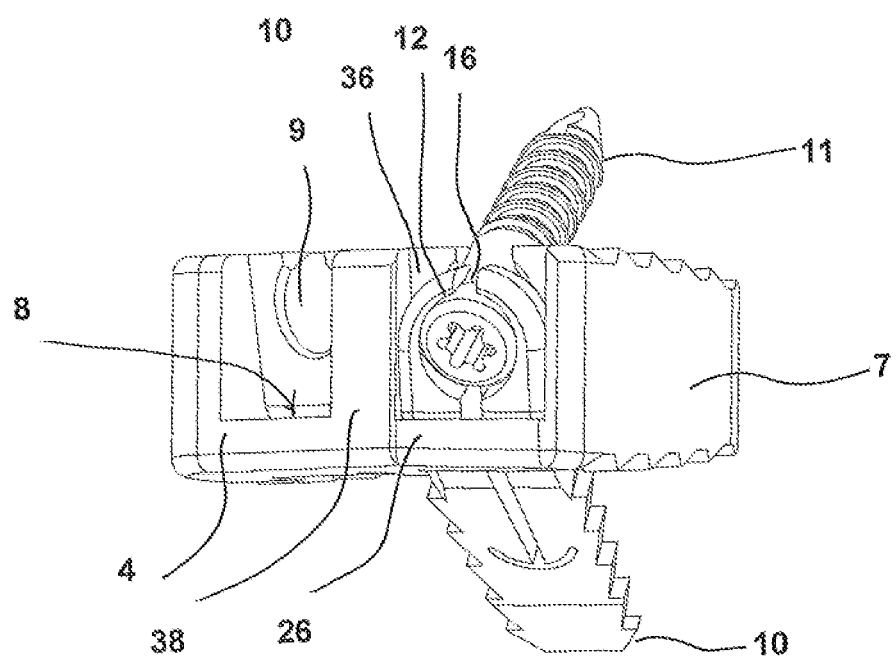
FIG. 4 represents a right anterolateral perspective view of the first exemplary embodiment of an implant according to the invention, with the two fastening elements represented in place in the anterolateral fastening holes of the volume.

According to the invention, the first 8 and second 9 inclined through-holes intersect so that one 11 of the first 10 and second 11 elongated fastening elements constitutes a first locking means for securing the other 10 of the first 10 and 11 second elongated fastening elements 11, once the first 10 and second 11 elongated fastening elements are respectively in place in the first 8 and second 9 inclined holes, as represented in FIGS. 3 and 4.

The upper 2 and lower 3 surfaces each comprise, in a known manner, serrations that are substantially parallel to one another and parallel to the front 4 and rear 5 faces of the volume 1, in which the sagittal section is created to prevent, in a known manner, displacement of the cage that is in reverse to its insertion between the vertebrae; in the example shown with the holes opening onto the front face of the volume, these are teeth 31 angled towards the front face of said volume, as represented in FIG. 5. The volume 1 can have any of the known shapes and external dimensions depending on the intervertebral implant and on requirements (lumbar in this example). The upper 3 and lower 2 surfaces may be slightly convex, as shown.

According to FIGS. 1-8, the volume 1 has the shape of an interbody cage which preferably and in a known manner has a central housing 15 opening onto the upper 3 and lower 2 faces, able to house a graft in contact with the two successive vertebral bodies (not shown) which the intervertebral spinal implant is to be inserted between.

In the example and as shown more particularly in FIG. 5, the first 8 and second 9 holes respectively form an angle preferably between 25° and 50°, preferably about 35°, with a transverse plane Pt of the volume 1. This angle represents the angle of insertion into the vertebra of the corresponding fastening element 10, 11.

The first 8 and second 9 holes open onto the anterofrontal portion 38 of the front face 4 of the volume 1.

The first 8 and second 9 holes advantageously and respectively have first 32 and second 33 longitudinal main axes for orienting and guiding the fastening elements, which are arranged in the same plane Ps, as is particularly visible in FIG. 6, and which form between them an angle preferably between 50° and 100°, preferably about 70°.

In the example shown in FIGS. 1-8, the inclined holes 8 and 9, and more particularly their constituent walls, intersect in an area of the volume 1 that is close to the front side 4 thereof, while the first 32 and second 33 main longitudinal axes of the holes 8, 9 intersect slightly forward of the front face 4, as shown in FIG. 5.

Figure 2:
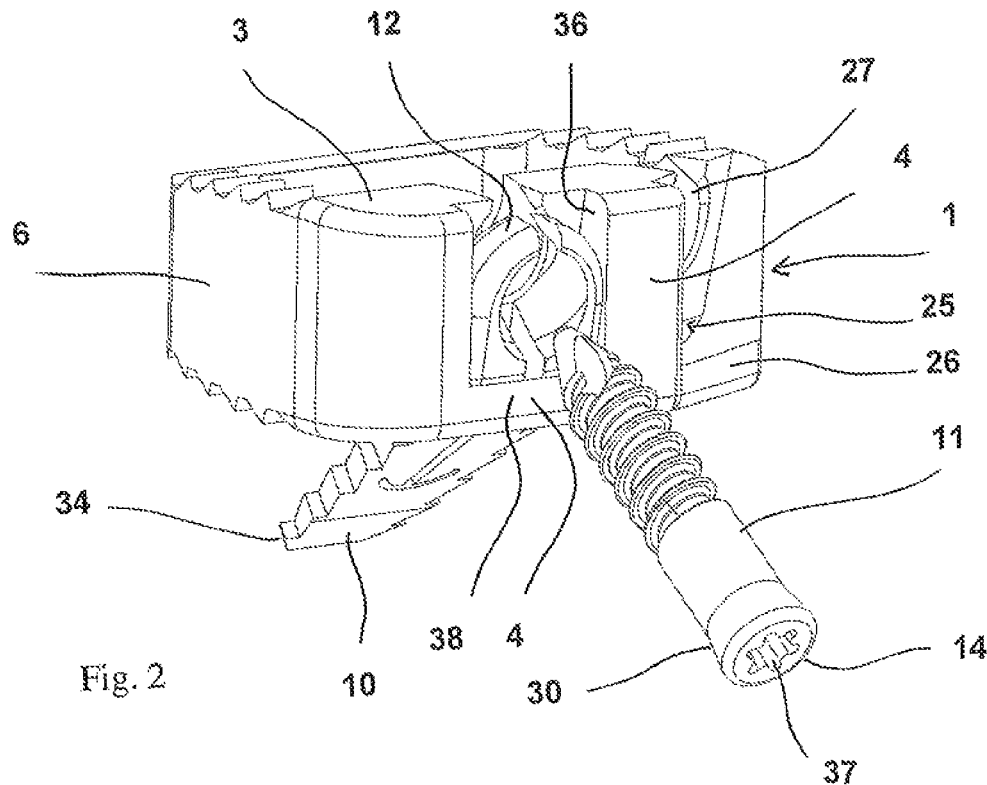
FIG. 2 represents a perspective view of the example of FIG. 1 with the two fastening elements represented, the fastening element represented in FIG. 1 being in place in its anterofrontal housing in the volume.

The elongated fastening elements 10, 11 enter their respective inclined holes 8 and 9 through the hole openings on the front side 4 of the volume 1, as shown in FIGS. 1 and 2 where the first elongated element 10 is shown ready to enter the first hole 8 (FIG. 1), and the second elongated element 11 is shown ready to enter the second hole 9.

As will be explained in more detail below, in the example in FIGS. 1 to 8, the first elongated element 10 is placed in its hole before the second elongated element 11, the latter locking the first elongated element 10 in its housing.

In the example in FIGS. 1 to 8, it is the second elongated fastening element 11 which constitutes the first locking means for securing the first elongated fastening element 10, once the first 10 and second 11 elongated fastening elements are respectively in place in the first 8 and second 9 inclined through-holes, via a first interlocking connection, the second elongated fastening element 11 acting as a stop for the first elongated fastening element 10, preventing it from backward longitudinal movement. FIG. 5 illustrates this situation, where one can see that the presence of the second fastening element 11 prevents the first fastening element from moving backward out of its hole 8 along the longitudinal axis 32, because the head of the second elongated fastening element 11 precludes such backward movement of the element 10.

As is particularly visible in FIG. 5, the central housing 15 opening onto the lower 2 and upper 3 faces is made so that the volume 1 still has sufficient constituent material to form the holes 8 and 9 in the front portion of the volume.

The intervertebral spinal implant illustrated in FIGS. 1 to 8 advantageously further comprises a second locking means 12 for securing, in the volume 1, the second elongated fastening element 11 constituting the first locking means securing the first elongated fastening element 10, once the first 10 and second 11 elongated bodies are respectively in place in the first 8 and second 9 inclined holes.

This second locking means 12 comprises, in the example of FIGS. 1 to 8, a frictional connection 30 connecting the second elongated fastening element 11 to the first elongated fastening element 10, as is detailed below in an example of this second locking means.

The second locking means 12 comprises, for example, a through-hole 13 created in the first elongated fastening element 10, which is aligned with the second inclined through-hole 9, into which the second elongated fastening element 11 is inserted, when the first elongated fastening element 10 is inserted into its inclined through-hole 8 and abuts against it, as shown in FIG. 5. This through-hole 13 and its arrangement coaxially to the second inclined hole 9 acts to block any backward movement of the first fastening element 10.

In addition, the second locking means 12 preferably comprises a conical assembly consisting of:
 the conically shaped through-hole 13, created in the first elongated fastening element 10, and
 a conical head 14 created at one end of the second elongated fastening element 11.

In the example of FIGS. 1 to 8, the second elongated fastening element advantageously consists of a screw 11.

Preferably, in this first embodiment of the implant, the first elongated fastening element consists of a pin 10 to be inserted longitudinally, while the second elongated fastening element 11 consists of the screw 11, the through-hole 13 being made in the pin-type elongated fastening element 10. This configuration allows engaging the second locking means 12 by rotating the screw 11 into the vertebra; when this screw 11 abuts longitudinally against said conical assembly, this determines the end of the screwing process, automatically locking the two fastening elements 10, 11 together.

The insertion pin 10 preferably comprises a radial slot 16 opening into the through-hole 13 of the pin 10, as shown in the figures and particularly in FIG. 6, such that when the screw 11 is inserted into its inclined hole 9, the portions of the pin 10 forming the through-hole 13 move apart at the end of the screwing process due to the pressure of the conical assembly between the conical head 14 of the screw 11 and the conical hole 13 of the pin 10, pressing it against the volume 1. The radial slot 16 may extend longitudinally over a large portion of the pin 10 and through its entire thickness, as shown for example in FIG. 6, in order to increase the effect of pressing the two resulting longitudinal arms of the pin 10 against the volume 1.

In order to obtain a compact and efficient auto-lock system for the two fastening elements 10, 11, as well as good stability of the implant once it is in place, the pin-type first elongated fastening element 10 preferably has a rectangular cross-section with a large width compared to the height, as shown. This rectangular cross-section of the pin 10 is preferably oriented so that the large width of the cross-section is perpendicular to the plane Ps formed by the longitudinal axes 32, 33 of the inclined holes 8 and 9. The pin 10 is tapered at its distal end 34 to provide better impact penetration into the bony element. The sides of the pin which are defined by the height of its rectangular cross-section preferably carry serrations to improve the retention of the pin 10 in the bony element. The pin 10 has, for example, a head 35 of rectangular cross-section that is an extension of the main body of the pin but forming an angle with said body, so that the head 35 of the pin 10 forms an angle of 0° to 20°, preferably about 10°, with the front face of the volume 1 or a frontal plane Pf of said volume, as is particularly visible in FIG. 5. The volume 1 comprises a seat 36 formed on the front face 4, which allows embedding the head 35 of the pin 10 within the volume 1 at the end of the insertion of said pin, and thus achieves the desired effect of the head 35, divided into two parts by the slot 16, pressing against the side walls of this seat 36 once the screw 11 is screwed into place. In the example shown in FIGS. 1 to 8, the seat 36 is a constituent part of both the hole 8 housing fastening element 10 and the hole 9 housing the second fastening element 11. In the example represented, and as is particularly visible in FIG. 5, only a small part of the head 14 of the screw 11 and the head 35 of the pin 10 protrudes beyond the seat 36 on the front face 4 of the volume 1.

The head of the screw 11 is provided with a means of a known type for engaging with screw insertion tools (not shown), such as a recess 37 that allows gripping and rotating the screw 11. The screw 11 is provided with a thread of a known type and an end that is preferably self-tapping, also of a known type for this type of application.

The implant represented in FIGS. 1 to 8 preferably further comprises:
a third inclined through-hole 25 formed in the volume 1 so that its two ends respectively open onto an anterolateral portion 26 of the front face 4 and onto the lower face 2 of the volume 1,
a fourth inclined through-hole 27 formed in the volume 1 so that its two ends respectively open onto the anterolateral portion 26 of the front face 4 and onto the upper face 3 of the volume 1.

The third 25 and fourth 27 inclined through-holes intersect such that the second elongated fastening element 11 constitutes a first locking means for securing the first elongated fastening element 10, once the first 10 and second 11 elongated fastening elements are respectively in place in the third 25 and fourth 27 inclined holes.

The third 25 and fourth inclined holes 27 are respectively identical to the first 8 and second 9 inclined holes, and are arranged in the same manner as the latter. These third 25 and fourth inclined holes 27 provide a second opportunity for fastening the implant with the first and second elongated fastening elements, additionally or alternatively, from an anterolateral access, while the first 8 and second 9 inclined holes provide anterofrontal access. It should be noted that FIG. 5 can also be considered a representation of a sagittal cross-section along the longitudinal axis of the fastening elements 10, 11 of FIG. 4, in which these fastening elements are implanted in the third 25 and fourth 27 inclined holes. The end openings of the first 8 and second 9 inclined holes in the anterofrontal portion 38 of the front face 4 on the one hand, and the end openings of the third 25 and fourth 27 inclined holes in the anterolateral portion 26 of the front face 4 on the other hand, are separate and do not overlap. The anterolateral portion 26 of the front face 4 forms an angle 38 with the anterofrontal portion of the front face 4, its value for example preferably between 15° and 35°, preferably 25°.

Figure 7:
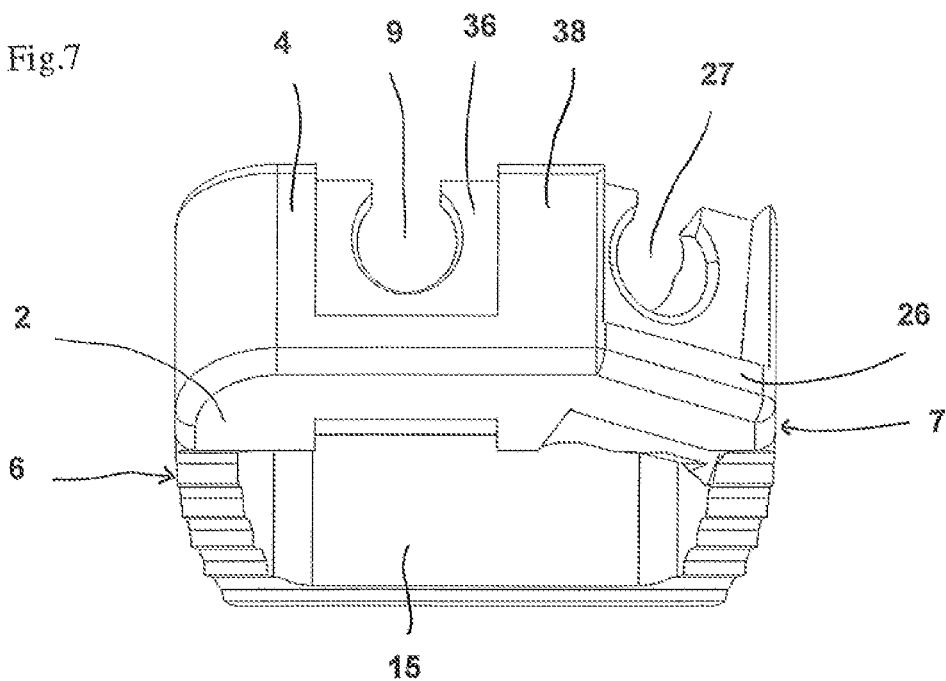
FIG. 7 represents a bottom perspective view along the axis of the second fastening hole, showing only the volume according to the first example of an implant shown in FIGS. 1 to 6.
Figure 8:
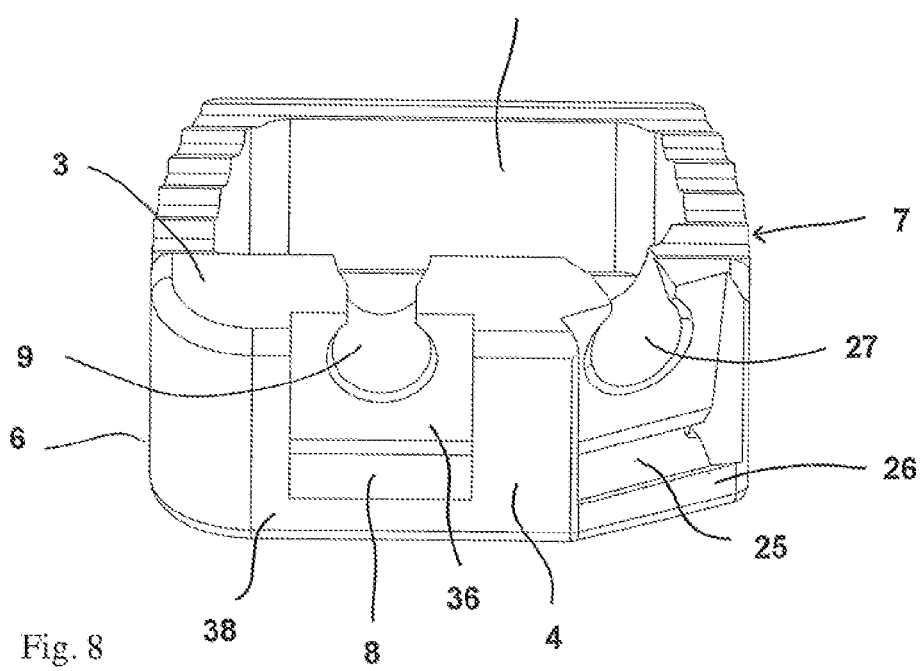
FIG. 8 represents a top perspective view along the axis of the first fastening hole, showing only the volume according to the first example of an implant shown in FIGS. 1 to 6.
Figure 9:
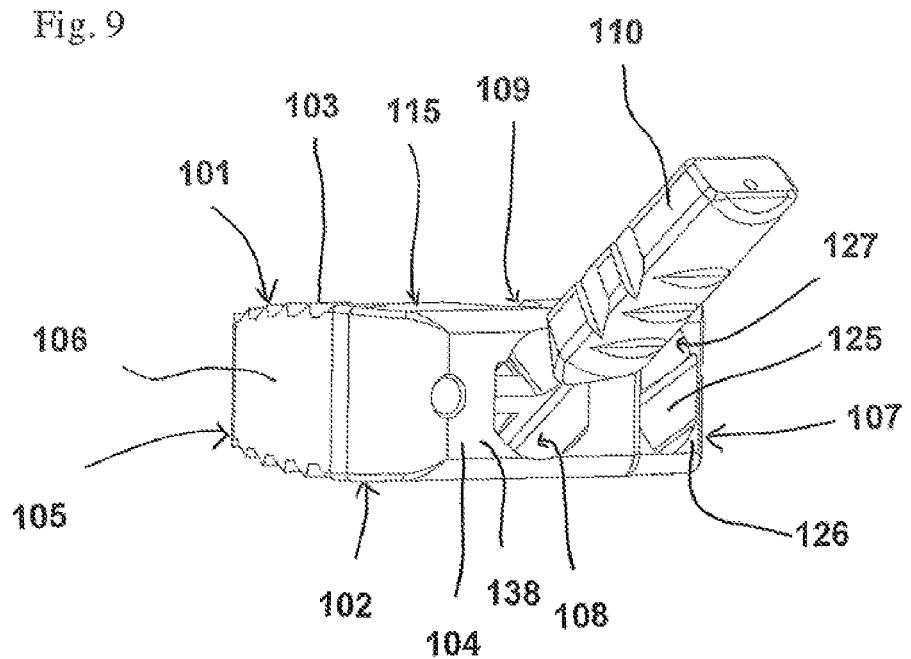
FIG. 9 represents a left anterolateral perspective view that is partial and exploded, of a second exemplary embodiment of an intervertebral spinal implant according to the invention, the view being described as partial because only one of the fastening elements is shown.
Figure 10:
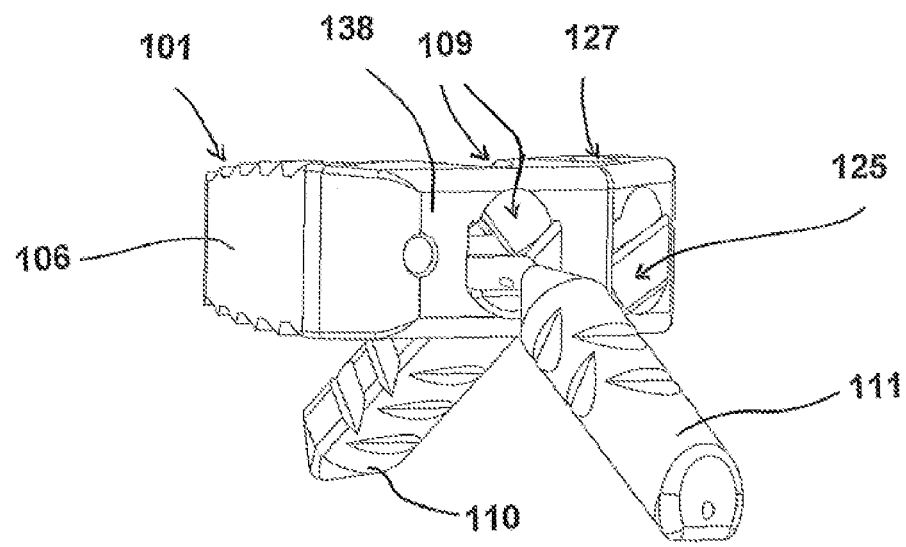
FIG. 10 represents a perspective view of the example of FIG. 9 with both fastening elements represented, the fastening element shown in FIG. 9 being in place in its anterofrontal housing in the volume.
Figure 11:
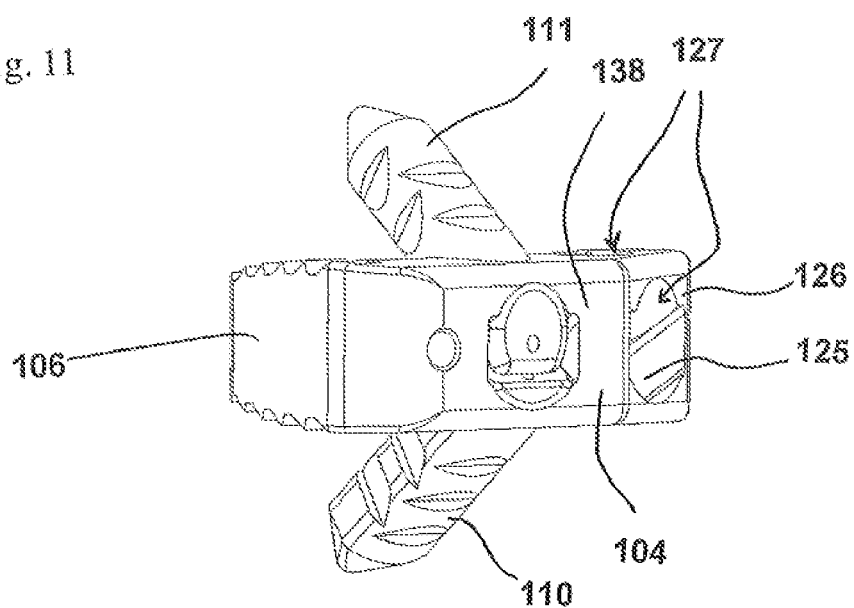
FIG. 11 represents a perspective view of FIG. 10, with both fastening elements shown in place in their respective anterofrontal housings in the volume.
Figure 12:
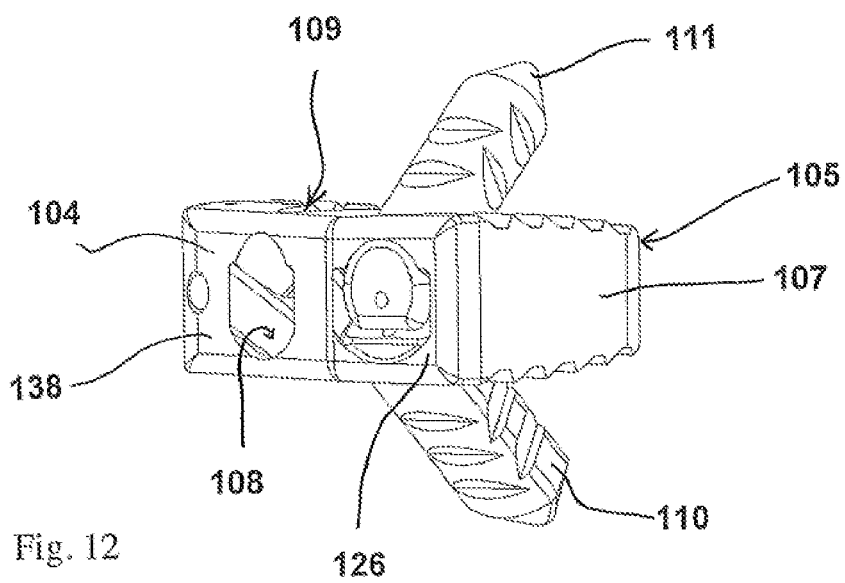
FIG. 12 represents a right anterolateral perspective view of the second exemplary embodiment of an implant according to the invention, with the two fastening elements represented in place in the anterolateral fastening holes of the volume.
Figure 17:
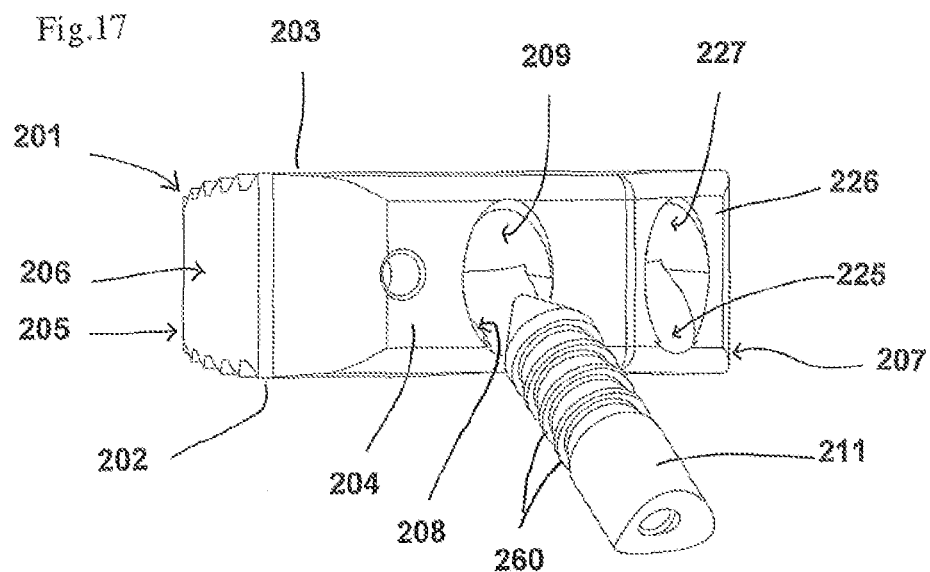
FIG. 17 represents a left anterolateral perspective view that is partial and exploded, of a third exemplary embodiment of an intervertebral spinal implant according to the invention, the view being described as partial because only one of the fastening elements is shown.
Figure 18:
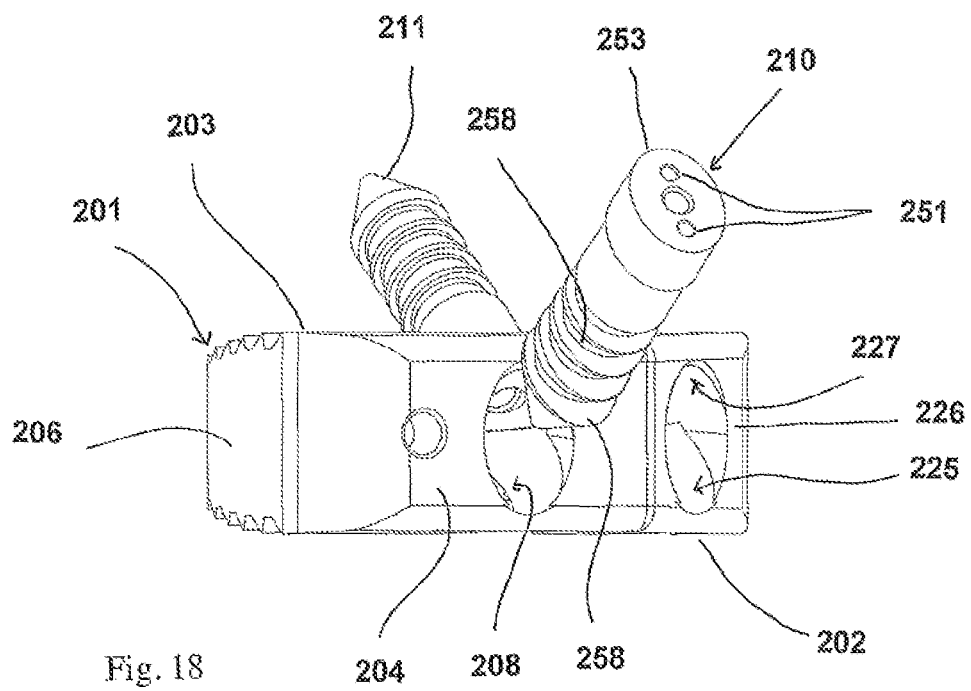
FIG. 18 represents a perspective view of the example of FIG. 17 with both fastening elements represented, the fastening element shown in FIG. 17 being in place in its anterofrontal housing in the volume.
Figure 19:
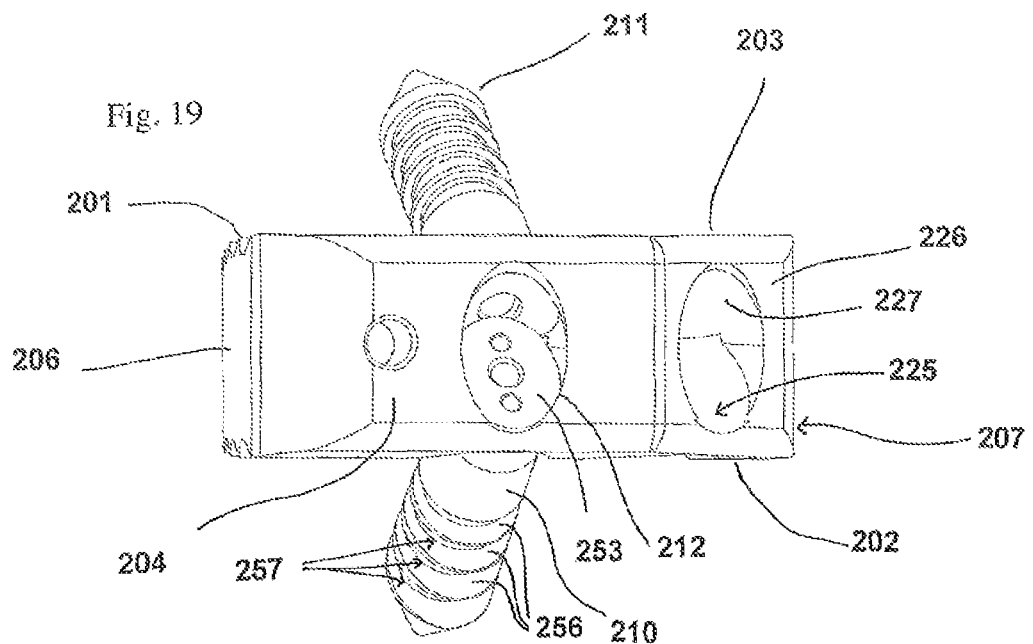
FIG. 19 represents a perspective view of FIG. 18, with both fastening elements shown in place in their respective anterofrontal housings in the volume, the first fastening element being shown after insertion but not locked.
Figure 20:
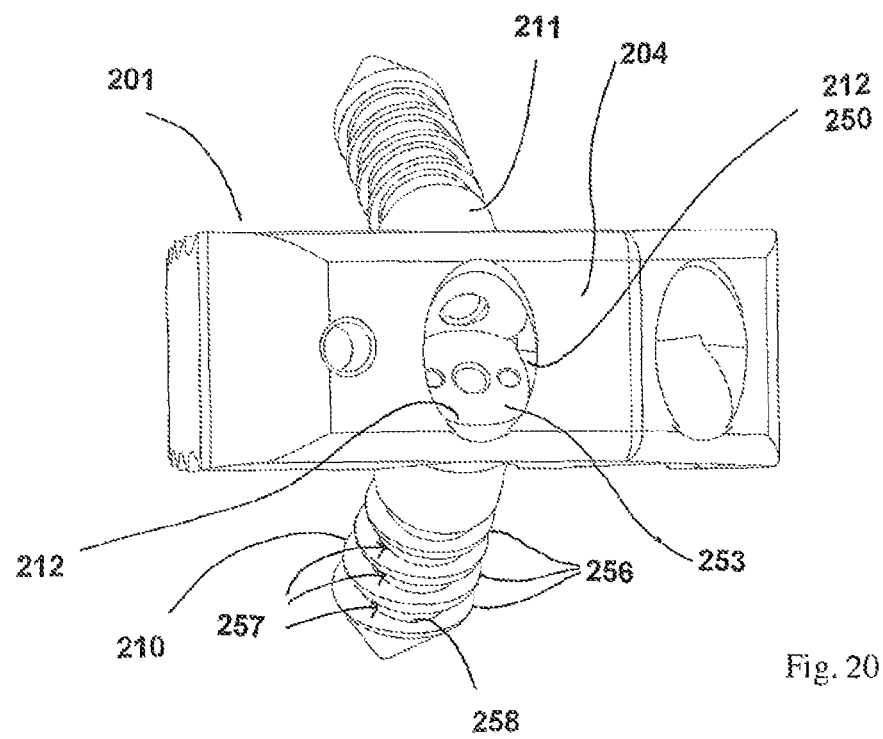
FIG. 20 represents a right anterolateral perspective view of the example according to FIG. 19, with the first fastening element shown in its locked position in the volume.
Figure 21:
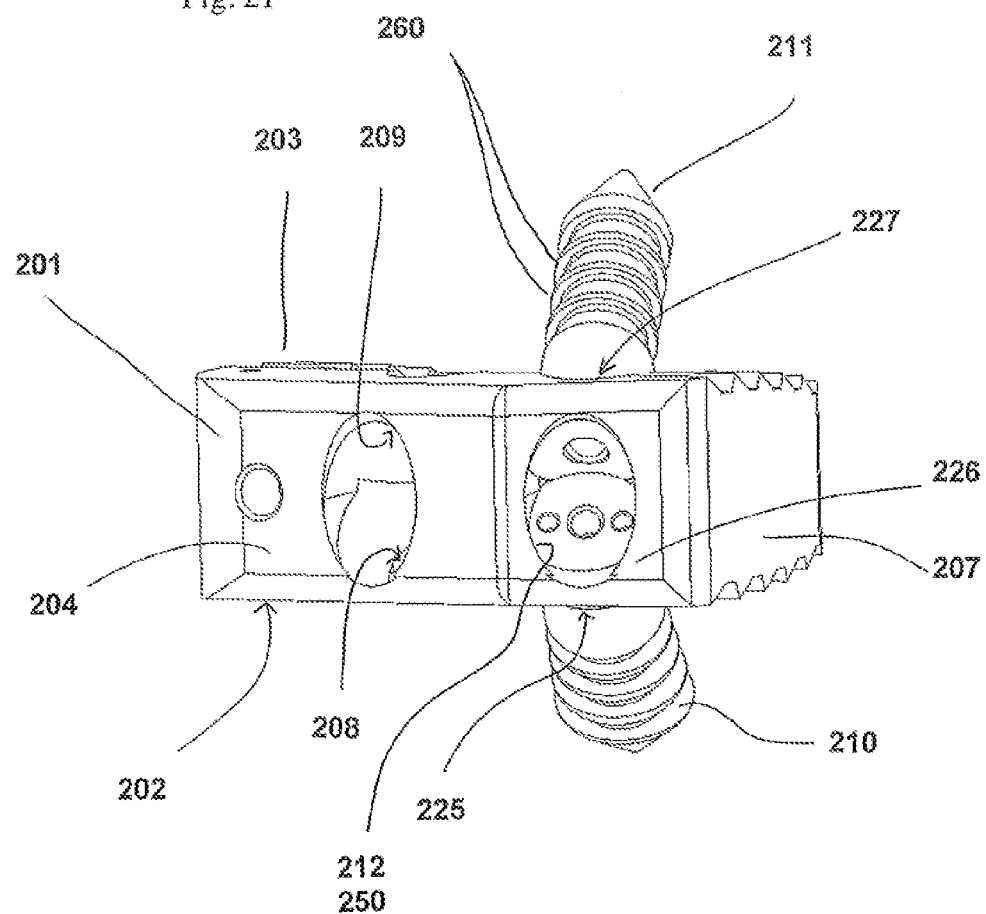
FIG. 21 represents a right anterolateral perspective view of the third exemplary embodiment of an implant according to the invention, with the two fastening elements represented in place in the anterolateral fastening holes of the volume, the first body being locked.

In FIG. 7, one can see the circular cross-section, open and smooth in this example, of the inclined second hole 9 which the screw 11 can slide into, up to its conical head 14, and in FIG. 8 one can see the rectangular enclosed and smooth cross-section of the inclined first hole 8 which the pin 10 can slide into until its head 35 abuts against the seat 36. The rectangular hole 8 with its seat 36 for the head of the pin 10, also having a rectangular cross-section, forms with the pin a very compact assembly which securely holds the cage relative to the lower vertebra. Hole 9 is partially open longitudinally for compactness and given the intersecting nature of the inclined holes 8 and 9. This longitudinal opening near the top of the inclined hole 9 is compensated for by the screw 11 passing through the pin 10 which thus contributes to the solidity of the connection between screw 11 and volume 1. It is understood, as mentioned above and as shown in FIGS. 7 and 8, that holes 25 and 27 have the same configuration.

The implant according to FIGS. 1 to 8 operates as follows:
the operator inserts the volume 1 between two vertebrae from an anterior access in a known manner, by means of an insertion instrument (not shown) such as a cage introducer, connected to the volume 1, for example after filling the housing 15 with a graft,
the operator then places the pin 10 by inserting it longitudinally from the front to the rear, by means of an insertion instrument (not shown) such as an impactor, via the opening in the front face 4 of the hole 8 or 25 for the pin 10, into the lower vertebral bony element (not shown), until the pin 10 abuts against the seat 36 of the hole 8 or 25 formed in the volume 1; at this stage of the implant installation, the hole 13 through the pin 10, arranged at a proximal end of said pin, is aligned with the hole 9 or 27 for the screw 11, formed in the volume 1,
the operator then inserts the screw 11 by screwing it in from the front to the rear by means of an insertion instrument (not shown) of known type, via the conical hole 13 of the pin 10 and via its hole 9 or 27 in the volume 1, until the conical head 14 of the screw 11 abuts against the corresponding conical hole 13 of the pin 10 which it presses against after tightening, the screw 11 and the pin 10 thus automatically locking each other in place in the volume 1.

The second exemplary embodiment of the intervertebral spinal implant according to the invention will now be described with the aid of FIGS. 9 to 16.

The second implant example shown in FIGS. 9 to 16 primarily differs from the first example shown in FIGS. 1 to 8 by the shape of the two elongated fastening elements and their respective cooperating parts of the implant volume, essentially their inclined holes. In this second example, the same reference numbers will be used as in the first example in FIGS. 1 to 8 for the same elements performing the same functions, but with the number 100 added. For the second example in FIGS. 9 to 16, one can therefore refer to what was said for these elements in the above description with reference to FIGS. 1-8.

According to this second example, the second locking means 112 as defined above comprises a form-locking connection 140 that fastens the second elongated fastening element 111 to the volume 101. The two elongated fastening elements 110 and 111 respectively consist of two insertion pins.

The first 110 and second 111 elongated fastening elements thus consist advantageously of first 110 and second 111 insertion pins, the form-locking connection 140 being achieved by means of a retaining member 141 formed in relief on the second insertion pin 111 and extending transversely beyond the free passage section, in the volume, of the second insertion pin 111 when the first pin 110 is in its end-of-insertion position, so as to provide a slight resistance to insertion, the retaining member 141 being designed so that it is able to:

deform elastically with the assembly consisting of the volume 101 and the first 110 and second 111 insertion pins during insertion of the second pin 111, so that the retaining member 141 and the second pin 111 which carries it pass through said free passage section, and cooperate at the end of insertion with a stop 142 formed on the volume 101, the assembly consisting of the volume 101 and the first 110 and second 111 insertion pins having elastically returned, in this end-of-insertion position, to its initial undeformed shape, as is particularly visible in FIG. 13.

The pins 110 and 111 have for example rounded or substantially rounded cross-sections, the first pin 110 as shown in the figures having straight side faces, their length connecting an upper face that is also flat and a rounded lower face. The second pin 111 has a substantially circular cross-section comprising a longitudinal flat section along its length. The outer surface of the pins 110 and 111 preferably includes external serrations for bony element retention, on their respective portions which project from the volume 101 at the end of penetration. The pins 110 and 111 have penetrating distal ends, for example pointed or substantially pointed.

As with the first example, the first 108 and second 109 holes advantageously and respectively have first 132 and second 133 longitudinal main axes for orienting and guiding the fastening elements, which are arranged in the same plane Ps, as is particularly visible in FIG. 14, and which form between them an angle preferably between 50° and 100°, preferably about 70°.

The holes 108 and 109 intersect in the front area of the volume 101, near the front face 104. The longitudinal axes 132, 133 of the holes 108 and 109 intersect slightly forward of the front face 104, as shown in FIG. 13. FIGS. 15 and 16 more particularly show the respective cross-sections of the second hole 109 and the first hole 108.

The proximal faces of the pins 110 and 111 are, for example, flat and inclined so as to be aligned or substantially aligned with the front face 104 of the volume 101 at the end of insertion, as is particularly visible in FIG. 13. The end of insertion of the pins 110 and 111 is respectively determined for example by the alignment of the proximal faces of the pins 110 and 111 with the portion of the front face concerned, meaning the anterofrontal portion 104 or the anterolateral portion 126 of the volume 101. This alignment is obtained, for example, by means of an impactor tool that inserts the pins.

The retention member 141 of the second pin 111 may, for example, consist of a sloping section in which the initial portion toward the distal end of the pin 111 is coincident with the flat undersurface of the pin 111, and in which the end portion toward the proximal end of the pin 111 forms a sharply angled section connecting this flat undersurface, appropriate for catching on the stop 142 formed on the volume 101, as shown in FIG. 13.

A similar retaining member 145 may advantageously be arranged on the first pin 110, particularly on its flat upper face, cooperating with a corresponding stop 146 formed on the volume 101, as shown in FIG. 13. The retaining member 145 can serve to maintain the first pin 110 during placement of the second pin 111 which then locks this first pin 110 in place when the proximal portion of the second pin 111 abuts against the first pin 110 at the end of insertion, as shown in FIGS. 11 to 14. After placement of the second pin 111, the retaining member 145 reinforces the connection between the first pin 110 and the volume 101.

The pins 110 and 111 are inserted longitudinally, for example by means of a tool such as an impactor (not shown), the first pin 110 being placed before the second pin 111 which will close off the entrance to the first hole 108 and thus prevent the first pin 110 from sliding backward once it is inserted. Generally, the impactor tool is used in an intrinsic manner to define the insertion stop for the two pins respectively.

The end of insertion of the pins 110 and 111 can be obtained when the proximal face of each of the pins in turn is flush with the front face 104 of the volume 101. At this point, a click is produced for each pin, corresponding to the return to the initial position of the assembly consisting of the volume 101 and pins 110, 111, having in this end-of-insertion position elastically returned to the initial position once each retaining member 141 and 145 in turn passes its respective stop 142 and 146 formed on the volume 101.

As with the first example, the volume 101 has two additional inclined holes 127 and 125 arranged in an anterolateral portion of the front face 104 of the volume 101, to allow anterolateral access for the pins.

The third exemplary embodiment of the intervertebral spinal implant according to the invention will now be described with reference to FIGS. 17 to 25.

The third implant example shown in FIGS. 17 to 25 primarily differs from the first example shown in FIGS. 1 to 8 by the shape and arrangement of the two elongated fastening elements and their respective cooperating parts of the implant volume, essentially their inclined holes. In this third example, the same reference numbers will be used as in the first example in FIGS. 1 to 8 for the same elements performing the same functions, but with the number 200 added. For this third example in FIGS. 9 to 16, one can therefore refer to what was said for these elements in the above description with reference to FIGS. 1 to 8.

According to this third example, the first 210 and second 211 elongated fastening elements are respectively in the form of first and second insertion pins. This differs from the first and second examples in that the second pin 211 which reaches the upper face 203 of the volume 201 is the first to be inserted, the first pin 210 which reaches the lower face 202 of the volume 201 being the second pin to be inserted.

In addition, this third example differs from the second example in that the second locking means 212 comprises an interlocking connection 250 obtained by rotating the first elongated fastening element 210 a quarter turn about its longitudinal axis after it is inserted longitudinally into its inclined through-hole 208, thus locking the second elongated fastening element 211 in this position in the volume 201.

Thus, in this third example, the second elongated fastening element 211 consists of a first insertion pin 211, and the first elongated fastening element 210 consists of a second insertion pin 210, the latter being provided with a head 253 constituting the interlocking connection 250 in cooperation with a seat in the volume 201 within which the head is pivoted at the end of insertion, said head 253 being provided with means 251 for engaging said head for rotation.

Preferably, the head 253 of the second pin 210 has an elliptical cross-section.

Figure 24:
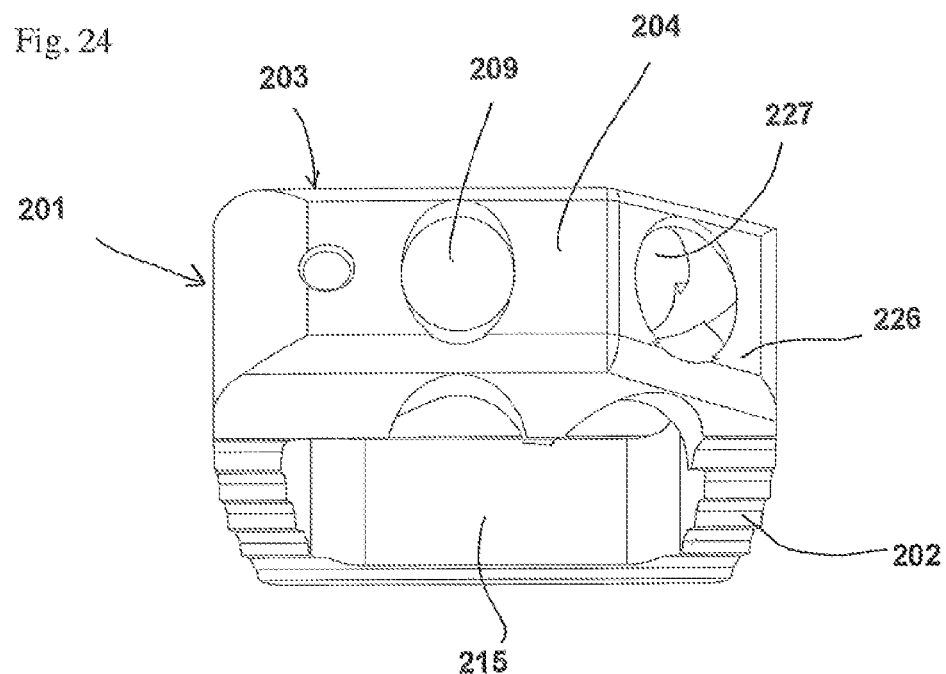
FIG. 24 represents a bottom perspective view along the axis of the second fastening hole, showing only the volume according to the third example of an implant shown in FIGS. 17 to 23.

The first insertion pin 211 has, for example, a cylindrical shape of circular cross-section with a distal portion for insertion into the bony element comprising circular serrations 260, and a substantially pointed distal end. The proximal end of the first insertion pin 211 has, for example, a concave cylindrical shape with a circular or elliptical cross-section, complementary to the shape of the second insertion pin 210 that will lie against it at the end of insertion of the latter. FIG. 24 shows the circular cross-section of the hole 209 that receives the pin 211.

The second pin 210 to be inserted has, for example, an elliptical cross-section at its proximal end, then a cross-section which grows wider toward the distal end while remaining elliptical and comprising alternating circumferential ribs 256 and cylindrical grooves 257, as indicated below.

Figure 25:
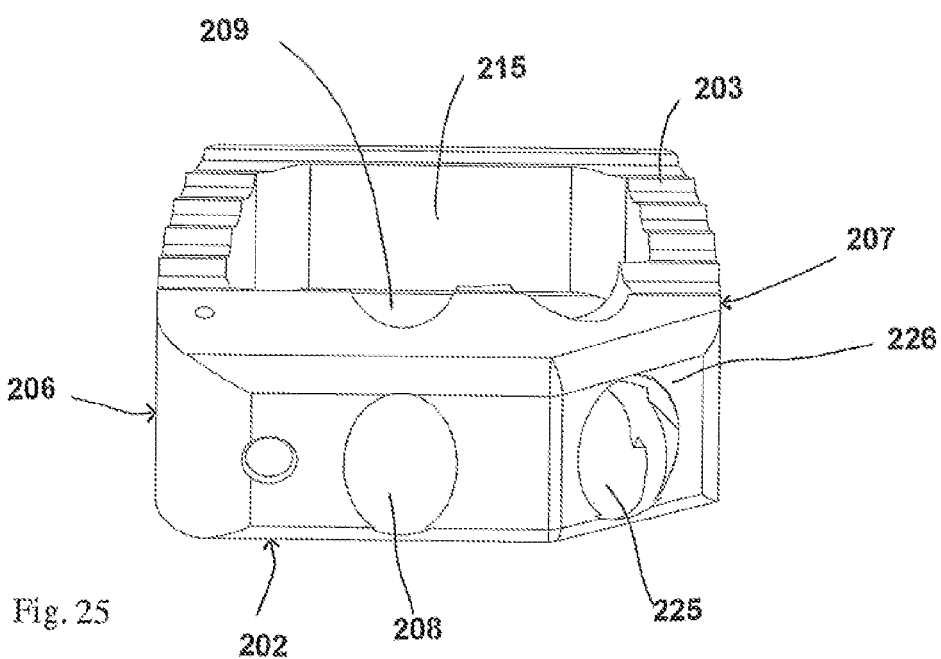
FIG. 25 represents a top perspective view along the axis of the first fastening hole, showing only the volume according to the third example of an implant shown in FIGS. 17 to 23.

At the end of insertion of pin 210, the head 253 is fully embedded in the volume 201. In order to lock the head 253 in the volume 201 by rotation, the hole 208 has an entry section in the front face 204 that is elliptical in shape, allowing the head 253 to enter the hole, as represented in FIG. 25. Near the rear of the hole 208 there is a circular seat which has a diameter at least equal to the width of the ellipse, which allows the elliptical head to rotate within this seat once the head has passed through the elliptical entry section. The remaining rear portion of the hole 208 has a cross-section that allows the pin to rotate, based on the chosen cross-section of the pin under its head.

Preferably, as is more particularly visible in FIG. 22, the first elongated fastening element 210 which will rotate a quarter turn about its longitudinal axis comprises a distal external portion 255 extending outside the volume 201 when said element is in the inserted position and able to pivot in its inclined through-hole 208, said distal external portion 255 being adapted for insertion into the adjacent vertebral body and comprising:
  a longitudinal central core 258, for example a core with a circular cross-section,
  a plurality of circumferential ribs 256 each extending in a plane transverse to said longitudinal central core 258, their circumference in the shape of an ellipse,
  a plurality of cylindrical grooves 257, each between two successive circumferential ribs 256.

It should be noted that this shape of the distal portion of the pivoting pin 210 may be used in other embodiments of the intervertebral implant in which an elongated fastening element is used, including implants whose holes for housing the fastening elements do not intersect, meaning the holes for housing the fastening elements are autonomous and independent.

As with the first and second exemplary embodiments, the first 208 and second 209 holes advantageously and respectively have first 232 and second 233 main longitudinal axes for orienting and guiding the fastening elements, which are arranged in the same plane Ps, as is particularly visible in FIG. 23, and which form between them an angle preferably between 50° and 100°, preferably about 70°.

The holes 208 and 209 intersect in the front area of the volume 201, near the front face 204. The longitudinal axes 232, 233 of the holes 208 and 209 intersect substantially at the front face 204, as represented in FIG. 22. FIGS. 24 and 25 show the respective cross-sections of the second hole 209 and the first hole 208.

The pins 210 and 211 are inserted longitudinally, for example by means of a tool such as an impactor (not shown), the second pin 211 being placed before the first pin 210 which will close off the entrance to the second hole 209 and thus prevent the second pin 211 from sliding backward once it is inserted. After inserting the pin 210 into its housing, for example by means of its head 253, it is rotated a quarter turn to lock it in place in the volume and prevent it from any movement that would reverse the insertion. Pin 210 acts as a stop for pin 211 and prevents the latter pin from leaving its housing and sliding backward, by means of an interlocking connection. Generally, the impactor tool is used in an intrinsic manner to define the insertion stop for the two pins respectively.

As with the first and second examples, the volume 201 has two additional inclined holes 227 and 225 arranged in an anterolateral portion of the front face 204 of the volume 201, to allow anterolateral access for the pins.

The implant represented in the figures, with its volume and fastening elements, can be made of a radiotransparent material, for example a thermoplastic such as PEEK (polyether ether ketone), or a radiopaque material, for example a metal material such as a biocompatible titanium-based alloy.

The invention claimed is:

1. An intervertebral spinal implant for insertion between two successive vertebral bodies, comprising:
  a volume defining at least:
    a lower face and an upper face, opposite one another and configured to be placed in contact with the two successive vertebral bodies respectively,
    a front face, a rear face, and two side faces, connecting the lower and upper faces,
  a first inclined through-hole formed in the volume and having two ends respectively open onto the front face and the lower face of the volume,
  a second inclined through-hole formed in the volume and having two ends respectively open onto the front face and the upper face of the volume,
  a first elongated fastening element for securing the volume, the first elongated fastening element having a length greater than a length of the first inclined through-hole and being configured to cooperate by longitudinal insertion into said first inclined through-hole from the front face in order to be implanted in the vertebral body adjacent to the lower face of the volume, and
  a second elongated fastening element for securing the volume, the second elongated fastening element having a length greater than a length of the second inclined through-hole and being configured to cooperate by longitudinal insertion into said second inclined through-hole from the front face in order to be implanted in the vertebral body adjacent to the upper face of the volume, wherein:

said first and second inclined through-holes intersect and one of said first and second elongated fastening elements constitutes a first locking means for securing the other of said first and second elongated fastening elements, once said first and second elongated fastening elements are respectively in place in the first and second inclined through-holes;

said first locking means includes a first interlocking connection, said one of said first and second elongated fastening elements acting as a stop for the other of said first and second elongated fastening elements, preventing the other of said first and second elongated fastening elements from backward longitudinal movement; and said intervertebral spinal implant further comprises a second locking means for securing, in the volume, said one of the first and second elongated fastening elements, wherein said second locking means comprises a form-locking connection of said one of the first and second elongated fastening elements to the volume or to the other of said first and second elongated fastening elements.

2. The intervertebral spinal implant according to claim 1, further comprising:

a third inclined through-hole formed in the volume and having two ends respectively open onto an anterolateral portion of said front face and onto said lower face of the volume, a fourth inclined through-hole formed in the volume and having two ends respectively open onto said anterolateral portion of said front face and onto said upper face of the volume, said third and fourth inclined through-holes intersect and the first locking means is for securing the other of said first and second elongated fastening elements, once said first and second elongated fastening elements are respectively in place in said third and fourth inclined through-holes.

3. The intervertebral spinal implant according to claim 1, wherein at least a first one of said first and second elongated fastening elements consists of a screw.

4. The intervertebral spinal implant according to claim 1, wherein said first and second elongated fastening elements are composed of first and second insertion pins, said form-locking connection including a retaining member formed in relief on the second insertion pin and which extends transversely beyond a free passage section, in the volume, of the second insertion pin when the first insertion pin is in an end-of-insertion position, so as to provide a slight resistance to insertion, said retaining member being configured to:

deform elastically with an assembly consisting of the volume and the first and second insertion pins during insertion of the second insertion pin, so that the retaining member and the second insertion pin pass through said free passage section, and cooperate at an end of insertion with a stop formed on the volume, the assembly consisting of the volume and the first and second insertion pins having elastically returned, in the end-of-insertion position, to an initial undeformed shape.

5. The intervertebral spinal implant according to claim 1, wherein the volume is an intervertebral cage having a central housing opening onto the lower and upper faces, and is adapted to house a graft in contact with the two successive vertebral bodies which said intervertebral spinal implant is to be inserted between.

6. An intervertebral spinal implant for insertion between two successive vertebral bodies, comprising:

a volume defining at least:

a lower face and an upper face, opposite one another and configured to be placed in contact with the two successive vertebral bodies respectively, a front face, a rear face, and two side faces, connecting the lower and upper faces, a first inclined through-hole formed in the volume and having two ends respectively open onto the front face and the lower face of the volume, a second inclined through-hole formed in the volume and having two ends respectively open onto the front face and the upper face of the volume, a first elongated fastening element for securing the volume, the first elongated fastening element having a length greater than a length of the first inclined through-hole and being configured to cooperate by longitudinal insertion into said first inclined through-hole from the front face in order to be implanted in the vertebral body adjacent to the lower face of the volume, and a second elongated fastening element for securing the volume, the second elongated fastening element having a length greater than a length of the second inclined through-hole and being configured to cooperate by longitudinal insertion into said second inclined through-hole from the front face in order to be implanted in the vertebral body adjacent to the upper face of the volume, wherein:

said first and second inclined through-holes intersect and one of said first and second elongated fastening elements constitutes a first locking means for securing the other of said first and second elongated fastening elements, once said first and second elongated fastening elements are respectively in place in the first and second inclined through-holes;

said first locking means includes a first interlocking connection, said one of said first and second elongated fastening elements acting as a stop for the other of said first and second elongated fastening elements, preventing the other of said first and second elongated fastening elements from backward longitudinal movement;

said intervertebral spinal implant further comprises a second locking means for securing, in the volume, said one of the first and second elongated fastening elements; and, said second locking means comprises a frictional connection of said one of the first and second elongated fastening elements to the other of said first and second elongated fastening elements.

7. The intervertebral spinal implant according to claim 6, wherein said second locking means comprises a through-hole in said one of said first and second elongated fastening elements, wherein when said one of said first and second elongated fastening elements is inserted in one of the inclined through-holes and abuts the volume, the one of the inclined through-holes through which is inserted said one of said first and second elongated fastening elements becomes aligned with the inclined through-hole into which the other of said first and second elongated fastening elements is inserted.

8. The intervertebral spinal implant according to claim 7, wherein said second locking means comprises a conical assembly that includes:
   said through-hole in said one of said first and second elongated fastening elements, which is conical in shape, and
   a conical/tapered head created at one end of the other of said first and second elongated fastening elements.

9. The intervertebral spinal implant according to claim 6, wherein:
   at least a first one of said first and second elongated fastening elements consists of a screw,
   a second one of said first and second elongated fastening elements consists of a pin to be inserted longitudinally,
   said second locking means comprises a through-hole in the pin,
   when said pin is inserted in one of the inclined through-holes and abuts the volume, the through-hole in said pin becomes aligned with the inclined through-hole into which the screw is inserted.

10. The intervertebral spinal implant according to claim 9, wherein:
   said second locking means comprises a conical assembly that includes:
      said through-hole in the pin, and
      a conical/tapered head created at one end of the screw,
   said through-hole in the pin is conical in shape,
   said pin comprises a radial slot opening into said through-hole of the pin, and
   when the screw is inserted into one of the inclined through-holes, portions of the pin forming the through-hole move apart due to pressure of the conical assembly between the conical head of the screw and the conical hole of the pin, pressing against the volume the portions of the pin forming the through-hole.

11. The intervertebral spinal implant according to claim 6, further comprising:
   a third inclined through-hole formed in the volume and having two ends respectively open onto an anterolateral portion of said front face and onto said lower face of the volume,
   a fourth inclined through-hole formed in the volume and having two ends respectively open onto said anterolateral portion of said front face and onto said upper face of the volume,
   said third and fourth inclined through-holes intersect and the first locking means is for securing the other of said first and second elongated fastening elements, once said first and second elongated fastening elements are respectively in place in said third and fourth inclined through-holes.

12. The intervertebral spinal implant according to claim 6, wherein at least a first one of said first and second elongated fastening elements consists of a screw.

13. The intervertebral spinal implant according to claim 6, wherein the volume is an intervertebral cage having a central housing opening onto the lower and upper faces, and is adapted to house a graft in contact with the two successive vertebral bodies which said intervertebral spinal implant is to be inserted between.

14. An intervertebral spinal implant for insertion between two successive vertebral bodies, comprising:
   a volume defining at least:
      a lower face and an upper face, opposite one another and configured to be placed in contact with the two successive vertebral bodies respectively,
      a front face, a rear face, and two side faces, connecting the lower and upper faces,
   a first inclined through-hole formed in the volume and having two ends respectively open onto the front face and the lower face of the volume,
   a second inclined through-hole formed in the volume and having two ends respectively open onto the front face and the upper face of the volume,
   a first elongated fastening element for securing the volume, the first elongated fastening element having a length greater than a length of the first inclined through-hole and being configured to cooperate by longitudinal insertion into said first inclined through-hole from the front face in order to be implanted in the vertebral body adjacent to the lower face of the volume, and
   a second elongated fastening element for securing the volume, the second elongated fastening element having a length greater than a length of the second inclined through-hole and being configured to cooperate by longitudinal insertion into said second inclined through-hole from the front face in order to be implanted in the vertebral body adjacent to the upper face of the volume, wherein:
   said first and second inclined through-holes intersect and one of said first and second elongated fastening elements constitutes a first locking means for securing the other of said first and second elongated fastening elements, once said first and second elongated fastening elements are respectively in place in the first and second inclined through-holes;
   said first locking means includes a first interlocking connection, said one of said first and second elongated fastening elements acting as a stop for the other of said first and second elongated fastening elements, preventing the other of said first and second elongated fastening elements from backward longitudinal movement;
   said intervertebral spinal implant further comprises a second locking means for securing, in the volume, said one of the first and second elongated fastening elements; and
   said one of the first and second elongated fastening elements has a longitudinal axis and said second locking means comprises an interlocking connection obtained by a quarter-turn rotation about its longitudinal axis of said one of the first and second elongated fastening elements after said one of the first and second elongated fastening elements is inserted longitudinally into one of the inclined through-holes, thus locking said one of the first and second elongated fastening elements in the volume.

15. The intervertebral spinal implant according to claim 14, wherein said one of said first and second elongated fastening elements consists of a first insertion pin, and the other of said first and second elongated fastening elements consists of a second insertion pin, the second pin having a head constituting the interlocking connection in cooperation with a seat in the volume within which the head is pivoted at an end of insertion, said head being provided with means for engaging said head for rotation.

16. The intervertebral spinal implant according to claim 15, wherein said head of the second pin has an elliptical cross-section.

17. The intervertebral spinal implant according to claim 14, wherein said one of the first and second elongated fastening elements that is rotated a quarter turn about its longitudinal axis comprises an outer portion which extends outside the volume when in an inserted position and is able to pivot within the inclined through-hole through which the one of the first and second elongated fastening elements, said outer portion being adapted for insertion into the adjacent vertebral body and comprising:
- a longitudinal central core,
- a plurality of circumferential ribs each extending in a plane transverse to said longitudinal central core and a periphery of the ribs forming an ellipse, and
- a plurality of cylindrical grooves, each between two successive circumferential ribs.

18. The intervertebral spinal implant according to claim 14, further comprising:
- a third inclined through-hole formed in the volume and having two ends respectively open onto an anterolateral portion of said front face and onto said lower face of the volume,
- a fourth inclined through-hole formed in the volume and having two ends respectively open onto said anterolateral portion of said front face and onto said upper face of the volume,
- said third and fourth inclined through-holes intersect and the first locking means is for securing the other of said first and second elongated fastening elements, once said first and second elongated fastening elements are respectively in place in said third and fourth inclined through-holes.

19. The intervertebral spinal implant according to claim 14, wherein at least a first one of said first and second elongated fastening elements consists of a screw.

20. The intervertebral spinal implant according to claim 14, wherein the volume is an intervertebral cage having a central housing opening onto the lower and upper faces, and is adapted to house a graft in contact with the two successive vertebral bodies which said intervertebral spinal implant is to be inserted between.

* * * * *